US012016527B2

(12) United States Patent
Geafer et al.

(10) Patent No.: US 12,016,527 B2
(45) Date of Patent: *Jun. 25, 2024

(54) VIDEO MEDIASTINOSCOPE AND A METHOD FOR ITS CONFIGURATION

(71) Applicant: KARL STORZ SE & Co KG, Tuttlingen (DE)

(72) Inventors: Lawrence Geafer, Tuttlingen (DE); Andreas Heni, Tuttlingen (DE); Markus Kupferschmid, Tuttlingen (DE); Daniel Ulmschneider, Tuttlingen (DE)

(73) Assignee: KARL STORZ SE & CO. KG, Tuttlingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/953,188

(22) Filed: Sep. 26, 2022

(65) Prior Publication Data
US 2023/0020728 A1 Jan. 19, 2023

Related U.S. Application Data

(63) Continuation of application No. 16/890,278, filed on Jun. 2, 2020, now Pat. No. 11,490,792.

(30) Foreign Application Priority Data

Jun. 3, 2019 (DE) ................... 10 2019 003 840.1

(51) Int. Cl.
A61B 1/00 (2006.01)
A61B 1/05 (2006.01)
(Continued)

(52) U.S. Cl.
CPC ...... A61B 1/00124 (2013.01); A61B 1/00066 (2013.01); A61B 1/05 (2013.01); A61B 1/0684 (2013.01); A61B 1/07 (2013.01)

(58) Field of Classification Search
None
See application file for complete search history.

(56) References Cited

U.S. PATENT DOCUMENTS 3,986,854 A * 10/1976 Scrivo .................... A61B 1/267
600/199
4,905,802 A 2/1990 Nishigaki et al.
(Continued)

FOREIGN PATENT DOCUMENTS

DE 102012202133 A1 8/2013
EP 1522253 A1 4/2005
(Continued)

OTHER PUBLICATIONS

Winter, A., German Search Report for German Patent Application No. 10 2019 003 840.1, dated Mar. 2, 2020, pp. 1-6, Munich.
(Continued)

Primary Examiner — John P Leubecker
(74) Attorney, Agent, or Firm — Honigman LLP; David N. Villalpando

(57) ABSTRACT

A video endoscope, more specifically a video mediastinoscope, and an associated method for its configuration, comprises an elongate rigid shaft and a handle detachably attached to a proximal end section of the shaft, wherein the shaft comprises an optics shaft comprising an imaging optics and an electronic image sensor, wherein the optics shaft and a plug connector housing arranged at a proximal end of the optics shaft form a hermetically sealed unit enclosing the imaging optics and the image sensor, and wherein the handle comprises a handle housing in which an electronics unit is accommodated, wherein the electronics unit is hermetically sealed.

17 Claims, 4 Drawing Sheets

(51) Int. Cl.
*A61B 1/06* (2006.01)
*A61B 1/07* (2006.01)

(56) References Cited

U.S. PATENT DOCUMENTS

| | | | | |
|---|---|---|---|---|
| 5,188,094 | A * | 2/1993 | Adair | A61B 1/05 600/122 |
| 5,217,001 | A * | 6/1993 | Nakao | A61B 1/00142 600/116 |
| 5,441,043 | A * | 8/1995 | Wood | A61B 1/313 600/109 |
| 5,599,278 | A * | 2/1997 | Hibbard | A61B 1/00142 600/198 |
| 5,609,561 | A | 3/1997 | Uehara et al. | |
| 5,810,713 | A * | 9/1998 | Rondeau | A61B 1/0008 600/133 |
| 6,004,263 | A | 12/1999 | Nakaichi et al. | |
| 6,095,970 | A | 8/2000 | Hidaka et al. | |
| 6,398,724 | B1 * | 6/2002 | May | A61B 1/00188 600/167 |
| 6,471,640 | B1 | 10/2002 | Frische et al. | |
| 7,063,663 | B2 | 6/2006 | Kazakevich | |
| 7,212,737 | B2 | 5/2007 | Dehmel et al. | |
| 8,152,715 | B2 | 4/2012 | Root et al. | |
| 8,556,807 | B2 | 10/2013 | Scott et al. | |
| 8,992,424 | B2 * | 3/2015 | Orbay | A61B 1/00108 600/183 |
| 9,107,573 | B2 | 8/2015 | Birnkrant | |
| 10,537,232 | B2 | 1/2020 | Heni et al. | |
| 11,490,792 | B2 * | 11/2022 | Geafer | A61B 1/07 |
| 11,611,725 | B2 * | 3/2023 | Tomatsu | A61B 1/0008 |
| 2003/0216616 | A1 | 11/2003 | Krupa | |
| 2005/0075539 | A1 * | 4/2005 | Schulz | A61B 1/00108 600/178 |
| 2005/0267335 | A1 * | 12/2005 | Okada | A61B 1/00183 600/173 |
| 2006/0258910 | A1 * | 11/2006 | Stefanchik | A61B 1/00135 600/101 |
| 2008/0114207 | A1 * | 5/2008 | Krupa | A61B 1/00068 600/178 |
| 2009/0253967 | A1 * | 10/2009 | Gill | A61B 1/07 600/249 |
| 2009/0292169 | A1 * | 11/2009 | Mitani | A61B 1/042 600/110 |
| 2010/0261961 | A1 * | 10/2010 | Scott | G02B 23/2476 600/111 |
| 2011/0018988 | A1 * | 1/2011 | Kazakevich | G02B 23/2484 348/E7.085 |
| 2013/0211199 | A1 * | 8/2013 | Navok | A61B 1/00096 600/176 |
| 2014/0206939 | A1 * | 7/2014 | Eisele | A61B 1/128 600/156 |
| 2014/0316194 | A1 * | 10/2014 | Rapp | A61B 1/00071 600/104 |
| 2014/0371530 | A1 | 12/2014 | Wieters et al. | |
| 2015/0065800 | A1 | 3/2015 | Jungbauer | |
| 2015/0289752 | A1 * | 10/2015 | Rachlin | A61B 1/00114 600/572 |
| 2015/0335230 | A1 * | 11/2015 | Tomatsu | G02B 23/2484 600/109 |
| 2016/0128549 | A1 | 5/2016 | Juergens | |
| 2016/0175006 | A1 * | 6/2016 | Dejima | A61B 1/00135 600/114 |
| 2017/0078583 | A1 * | 3/2017 | Haggerty | H04N 23/55 |
| 2017/0168287 | A1 * | 6/2017 | Lietzau | G02B 23/2453 |
| 2017/0209027 | A1 * | 7/2017 | Raj | A61B 1/00034 |

FOREIGN PATENT DOCUMENTS

| | | |
|---|---|---|
| EP | 2756791 A2 | 7/2014 |
| EP | 2792292 A1 | 10/2014 |
| EP | 3482673 A1 | 5/2019 |
| EP | 3513705 A1 | 7/2019 |
| WO | 2011142989 A1 | 11/2011 |

OTHER PUBLICATIONS

Mäki-Mantila, M, European SearchReport, App 20176444.6, dated Oct. 7, 2020; pp. 1-6; Munich.

* cited by examiner

VIDEO MEDIASTINOSCOPE AND A METHOD FOR ITS CONFIGURATION

CROSS REFERENCE TO RELATED APPLICATIONS

This application is a continuation of U.S. patent application Ser. No. 16/890,278, filed Jun. 2, 2020, entitled "Video endoscope and method for configuring a video endoscope," which claims priority to German Patent Application No. 102019003840.1 filed Jun. 3, 2019, entitled "Video endoscope and method for configuring a video endoscope,", both of which are incorporated herein by reference.

Further features of the video endoscope are disclosed in German Patent Application No. 102019003842.8, entitled "Endoscope and method for manufacturing an endoscope" and German Patent Application No. 102019003839.8, entitled "Endoskop, Verfahren zum Betreiben eines Endoskops sowie Verfahren zum Herstellen eines Endoskops" both filed on Jun. 3, 2019, and both incorporated herein by reference.

FIELD OF THE INVENTION

The present invention relates to a video endoscope comprising an elongate rigid shaft and a handle attached to a proximal end section of the shaft, wherein the shaft comprises an optics shaft comprising an imaging optics and an electronic image sensor. Further, the invention relates to a method for configuring a video endoscope.

BACKGROUND OF THE INVENTION

Endoscopes for medical or non-medical applications have an elongate shaft configured for being introduced into an internal cavity of a human or animal body or another object to be examined. In a distal (i.e. distant from a user) end section of the shaft an imaging optics is arranged for generating an image of an object field in the cavity of the body or object. Further, the endoscope has a handle attached to a proximal (i.e. close to a user) end section of the shaft. In video endoscopes, which also are denoted electronic endoscopes, the generated endoscopic image is picked up by an electronic image sensor. According to a widespread design, the elongate shaft is rigid, and the imaging optics and the electronic image sensor are contained in an optics shaft arranged in the shaft of the endoscope.

Reusable medical endoscopes require cleaning and sterilization after each use. During sterilization the endoscope is exposed to chemically aggressive media and/or, in an autoclave process, to high temperature and pressurized steam. On the other hand, video endoscopes comprise delicate and expensive optical and electronic components which need to be protected against contamination, in particular, against moisture that may intrude into the endoscope in a sterilization process. Frequently, endoscopes are designed to be disassembled for cleaning and sterilization, such that the different parts can be subjected to different sterilization processes, or some parts are protected by a sterile cover during a medical endoscopic intervention. Further, it is known to enclose optical and electronic components of an endoscope in a hermetically sealed chamber.

As disclosed in U.S. Pat. No. 6,083,151, a medical instrument has a tube-like element, a handle bent-off from the tube-like element, an endoscope having a shaft, a camera module connected to the endoscope, a light pipe and a guide provided on the tube-like element for receiving the shaft of the endoscope. The endoscope is provided with two coupling elements extending in a direction of the handle and into an inside of the handle, one of the coupling elements being coupled to the light pipe and another of the coupling elements being coupled to the camera module, and the camera module being disposed inside of the handle. After completion of an operation, the medical instrument is disassembled for sterilizing the different parts.

According to US 2014/0371530 A1, an endoscope shaft of a sideways viewing video endoscope comprises a tube that hermetically encloses the elements of the video endoscope that are essential for viewing. The shaft is closed at the distal end with an oblique window. The proximal end of the tube is closed by an insulating plate or a hermetic feed-through formed as a glass mold, and is penetrated by contact pins.

U.S. Pat. No. 7,063,663 B2 discloses an endoscopic system that includes an endoscope and an illumination assembly connected to a proximal body of the endoscope. The illumination assembly includes a solid-state light source assembly that provides illumination to a working area from multiple LEDs. A fiber-optic bundle conveys light from the solid state light source assembly to a distal end of the endoscope. At the interface of the solid state light source, the fiber-optic bundle is epoxied into a bushing, thereby creating a hermetic seal. However, it has turned out that it can hardly be completely avoided that traces of moisture pass through a sealed feed-through of a bundle of glass fibers in an autoclaving procedure.

In U.S. Pat. No. 9,107,573 B2 a flexible endoscope is disclosed comprising a handle having a first sealed enclosure, a flexible shaft having a second sealed enclosure, and a coupling mechanism releasably attaching the handle to the proximal end of the flexible shaft. In the second sealed enclosure an illumination unit and an imaging unit are disposed. A check valve is mounted on a proximal end of the flexible shaft, the check valve being configured to connect an interior of the second sealed enclosure to outside. The first and second sealed enclosures seal off fluid-tight internal components of the handle and the flexible shaft from outside in a coupled state and a decoupled state of the endoscope. Flexible endoscopes, however, are generally not subjected to an autoclave, and thus do not face the same challenges for sterilization as an autoclavable rigid endoscope.

Video endoscopes, in particular rigid video endoscopes, are subject to high requirements regarding usability, handling, and sterilization. Prior art rigid video endoscopes have shown to be non-optimal in these respects. In particular, in most such prior art endoscopes some components are not autoclavable and need a treatment different from that of other components, which imposes additional working steps and may incorporate potential risks. Moreover, in case of damage or malfunction of one of the optical and electronic components, the endoscope as a whole must be replaced or sent to the manufacturer for service, thereby increasing cost and instrumentation downtimes.

It is therefore an object of the present invention to provide an endoscope in which the above mentioned drawbacks are largely avoided. In particular, it is an object of the invention to provide a rigid video endoscope having improved autoclavability and serviceability. It is a further object of the present invention to provide a corresponding to method for configuring an endoscope.

BRIEF DESCRIPTION OF THE INVENTION

In accordance with the present invention a video endoscope comprises an elongate rigid shaft and a handle arranged at a proximal end section of the shaft. The video endoscope preferably is a medical endoscope, for example a video mediastinoscope, the rigid shaft being configured for being inserted into an internal body cavity of a human or an animal through a natural or an artificially created orifice. The shaft may comprise a rigid outer tube made of a metallic material, for example of stainless steel. Preferably the shaft is straight or approximately straight, but may be curved in some embodiments.

The handle is detachably attached, directly or indirectly, to the proximal end section of the shaft, the shaft and the handle preferably forming a rigid, but detachable unit. In the present context, the term "detachable" includes, in particular, being configured for disassembly requiring special tools, but without breaking or destruction of connecting element. The handle may be arranged at an angle to a longitudinal axis of the shaft, preferably at approximately a right angle. The handle preferably is configured for being gripped by a user, or as a part of a hand grip configured for being gripped by a user, with one hand. The user is, in particular, a surgeon employing the video endoscope in a medical endoscopic intervention. The handle may exhibit control elements to be operated by the user with fingers of the same hand.

The elongate rigid shaft of the video endoscope comprises an optics shaft that preferably extends parallel to a longitudinal axis of the shaft of the endoscope and may have a length approximately equal to or somewhat less than a length of the shaft of the endoscope. For clarity, the shaft of the video endoscope is denoted "endoscope shaft" in the following. The optics shaft preferably comprises an elongate, rigid tube. Within the optics shaft are contained an imaging optics and an electronic image sensor, for example a CCD or a MOSFET image sensor. The imaging optics is configured to generate an image of an object field in the body cavity to be observed on a sensor face of the electronic image sensor, the electronic image sensor generating an electric image signal. Preferably, the imaging optics and the electronic image sensor are arranged in a distal end section of the optics shaft.

In accordance with the present invention, the video endoscope comprises a plug connector housing arranged at a proximal end of the optics shaft. The plug connector housing may be a part of the endoscope shaft or attached to the proximal end section of the endoscope shaft. The optics shaft and the plug connector housing form a hermetically sealed unit which in the following is denoted "optics unit". At its distal end, the optics shaft may be hermetically sealed by a cover glass. At its proximal end, the optics shaft is connected in a hermetically sealed manner to the plug connector housing, thus forming a hermetically sealed chamber in which the imaging optics and the image sensor are housed. Further, the hermetically sealed chamber of the optics unit may house mechanical elements for mounting the imaging optics and the image sensor, for example, and electric lines for connecting the image sensor to a plug connector comprised by the plug connector housing and, further, to electronic circuitry of the video endoscope (see below).

In the present context, a "hermetic" seal means a tight seal that prevents the exchange or at least the intrusion of substances even under increased outside pressure, in particular a vapor-tight seal that prevents the intrusion of water vapor during an autoclaving procedure involving, for example, a temperature of 134° C. and a pressure of 2 bar. A hermetic seal may be provided, for example, by positive substance jointing of impermeable materials, for example by welding, soldering or adhering with suitable adhesive. Thus, for example, a closed casing formed by metallic walls and other elements inserted into the walls in a hermetically sealed manner may encase a hermetically sealed chamber.

Further in accordance with the present invention, the handle comprises a housing which for clarity is denoted "handle housing" in the present application. Within the handle housing an electronics unit is accommodated. Preferably the electronics unit is releasably arranged in the handle housing such that it can be removed from the handle housing at least when the handle is detached from the shaft. The electronics unit comprises electronic circuitry of the video endoscope, for example electronic circuitry for supplying electric energy to the image sensor and for controlling the image sensor, and/or for pre-processing of image signals provided by the image sensor. To this end the electronic circuitry is electrically connected to the image sensor. The electronic circuitry of the electronics unit may serve to supply energy to and/or control further electric or electronic components of the video endoscope, such as an internal light source of the endoscope.

The electronics unit is a hermetically sealed unit. The electronic circuitry is enclosed in a hermetically sealed chamber of the electronics unit. The hermetically sealed chamber may contain further elements, for example mechanical elements for mounting a PCB comprising the electronic circuitry and/or heat conducting materials for dissipating excess heat generated by the circuitry. The electronics unit is enclosed in the handle housing and can be removed from the handle housing, wherein removal may require special tooling.

Thus, the video endoscope comprises at least two hermetically sealed units, which are the optics unit comprised at least partially by the shaft, and the electronics unit contained in the handle. Both hermetically sealed units can be detached from each other by detaching the handle from the shaft, and may be connectable to each other by attaching the handle to the shaft. To this end the handle and the shaft may comprise coupling elements for mechanically coupling the handle and the shaft, and electric connectors and electric lines for electrically connecting the optics unit to the electronics unit. The video endoscope may comprise further elements and/or units, which may be part of the shaft or connected to the shaft, or may be part of the handle or connected to the handle.

Due to the video endoscope comprising a hermetically sealed optics unit and a separate, hermetically sealed electronics unit, both being separable from each other by detaching the handle from the shaft, the video endoscope can be easily detached for service purposes. In particular, in case of malfunction or damage of one of the units, only the respective one needs to be replaced, while the other unit may remain in use. Moreover, both units may be connectable to each other by connecting the handle to the shaft. The video endoscope may have a modular design, such that various endoscope shafts and optics units configured for different applications may be combinable with a single electronics unit and/or a single shaft and optics unit may be combinable with various electronics units of different types. The video endoscope therefore provides improved serviceability and versatility. Moreover, the compartmentalized design of the video endoscope facilitates cleaning and sterilization. Due to the optics unit and the electronics unit each being hermetically sealed, the optics unit and the electronics unit may be designed to be autoclavable, and thus all components of the video endoscope may be autoclavable.

According to a preferred embodiment of the invention, the endoscope shaft comprises a longitudinally slotted tube, which is denoted "shaft tube" in the following, and the optics shaft is fixedly or rigidly connected to the tube. The optics shaft may be, for example, soldered to the shaft tube on an inner surface of the tube or be inserted into a longitudinal bore in a wall of the shaft tube. In this way a compact and robust arrangement of the endoscope shaft and the optics shaft can be achieved. In particular, the video endoscope may be a video mediastinoscope, the longitudinally slotted tube forming a mediastinoscope spatula. The imaging optics of the optics shaft is preferably arranged for endoscopic view of a working space formed by a distal end of the shaft tube.

Preferably, at least one plug connector is integrated in the plug connector housing in a hermetically sealed manner, for example by inserting the plug connector into a form-fitting opening of the plug connector housing and adhering and sealing the plug connector in the opening by a suitable adhesive. Most preferably, the plug connector itself is a hermetic plug connector, for example a glass-mold plug connector comprising a multiplicity of pins penetrating a glass base in a hermetically sealed manner, providing electric connection into and out of the hermetically sealed chamber. Thus, in a simple and safe manner, an electrical connection between the electronic image sensor and outside electronics, which are outside the hermetically sealed chamber of the optics unit, can be provided.

In a further preferred manner, the electronics unit comprises at least one plug connector. In particular, the electronics unit comprises a casing in which the at least one plug connector is integrated in a hermetically sealed manner, for example inserted into a form-fitting opening and adhered and sealed by a suitable adhesive. The plug connector of the electronics units provides an electric connection to the image sensor and may provide connection to further electric or electronic elements of the video endoscope, such as a light source and/or one or more control elements. The plug connector may also provide an electric connection to an external supply and control system. In a most preferred manner, the electronics unit comprises at least two hermetically sealed plug connectors, a first plug connector forming a connection to internal electric or electronic components of the video endoscope, and a second connector providing connections to an external supply and control system.

According to a preferred embodiment of the invention, the handle is detachably attached to a head piece of the endoscope shaft. The head piece may be rigidly connected to a proximal end section of a shaft tube, thus forming a unit that in the present context is denoted the endoscope shaft. The head piece may protrude in a lateral direction from the endoscope shaft and may comprise a mechanical coupling element for holding the electronics unit and/or the handle housing. The head piece may accommodate the plug connector housing of the optics unit and/or further components of the video endoscope. The electronics unit and the handle housing may each be detachably attached to the head piece of the shaft of the video endoscope, or the electronics unit may be connected to the head piece and the handle housing connected to the electronics unit, for example. The endoscope shaft including the head piece, the electronics unit and the handle housing may be considered three separate modules that can be disassembled for service and attached to each other in various combinations, thus improving serviceability and versatility.

Most preferably, the electronics unit is enclosed in the handle housing, the handle housing is detachably fixed to the electronics unit and the electronics unit is detachably fixed to the head piece of the endoscope shaft such that a first fixation element for fixing the electronics unit to the head piece is operable only when the handle housing has been removed. The handle housing may be held on the electronics unit with at least one second fixation element. Thus, for example, the handle housing may be fixed to the electronics unit by a screw accessible from the outside, and the electronics unit may be fixed by means of one or more screws to the head piece of the shaft which are accessible only with the housing having been removed. In addition to mechanical fixation, detachable electrical connections may be provided at least between the electronics unit and the optics unit, for example by plug connectors and flexible boards or other electric lines. Thus a simple and safe connection of the handle and the electronics unit to the endoscope shaft can be provided. Further, in a most preferable manner, the second fixation element for mounting the handle housing to the electronics unit is operable only with special tooling. In this way unauthorized access to internal components of the video endoscope can be precluded.

According to a further preferred embodiment, the shaft of the video endoscope or the head piece comprises a light source for generating an illumination radiation, the light source being arranged outside the hermetically sealed optics unit formed by the optics shaft and the plug connector housing, and the endoscope shaft comprises a light guide configured for transmitting the illumination radiation generated by the light source to a distal end section of the shaft for illuminating an object field in the body cavity or in a working space to be observed. The light guide preferably is formed by a glass fiber bundle. Further preferably, a proximal end of the light guide is optically coupled to the light source, and the proximal end of the light guide and the light source are embedded in a sealing compound, for example in a suitable adhesive. In this way the light source can be sealed in a simple way against moisture, at least to a large degree. The light source preferably is formed by one or more light-emitting diodes (LEDs) mounted on a carrier element. The light source may be electrically connected to the electronics unit and supplied with electric energy by the electronics unit. Due to the video endoscope comprising a light source, no external light source is required. Moreover, in accordance with the present embodiment, the light source is located outside the optics unit, and thus any risk of water vapor entering into the hermetically sealed chamber of the optics unit along the optical fibers of a light guide can be safely avoided. In this way handling and durability of the video endoscope can be improved.

Preferably one or more control elements are arranged on the handle housing, the control elements being electrically connected to the electronics unit, to the image sensor and/or to the light source. The one or more control elements may be arranged on a PCB integrated into the handle housing. The control elements and the PCB are located outside the electronics unit and thus outside the hermetically sealed chamber of the electronics unit, thus avoiding any risk of leakage of the hermetically sealed chambers. The control elements permit control of the functionality of the video endoscope.

Most preferably, the video endoscope as a whole is embodied as a sealed unit, in particular the endoscope shaft and the handle attached to the endoscope shaft form a sealed unit. To this end, sealing elements can be provided between the handle and the endoscope shaft or, in particular, between the handle housing and a housing of the head piece of the shaft, to seal the endoscope as a whole when the handle is attached to the endoscope shaft. Such sealing permits improved cleaning and sterilization, although the sealing may not be a hermetic seal. Thus, the small amounts of moisture may enter into the video endoscope during autoclaving procedures, but not into the hermetically sealed optics and electronics units. Moreover, a light source arranged in the video endoscope, but outside the hermetically sealed units, can be protected from moisture to a large degree by embedding the light source and the proximal end of the light guide in a sealing compound, as mentioned above. Thus, the video endoscope can be cleaned without having to be disassembled, thereby facilitating handling in cleaning and sterilization.

According to a particularly preferred embodiment, the video endoscope in total is configured to be autoclavable. To this end, the mechanical, optical, electrical and electronic components of the video endoscope, including plastic materials and adhesives, are chosen such that they resist the temperatures of an autoclave process without damage. Moreover, at least the optics unit and the electronics unit are configured to resist the increase pressure encountered in the autoclave process, maintaining the respective hermetic seals. The video endoscope in total may enclose a sealed compartment including the optics unit, the electronics unit, and further components, such as a light source, for example. This sealed compartment may not be hermetically sealed. In this case, as traces of moisture may enter during cleaning, sterilization and autoclaving, the light source and other components exposed to such contamination may be separately sealed, for example by embedding into a sealing compound. Thus a reusable video endoscope is provided that can be cleaned and sterilized by autoclaving, without needing to be disassembled. Thereby handling and durability can be further improved.

According to a further aspect of the invention, a method is provided for configuring a video endoscope, in particular a video endoscope as described above. In accordance with the method, an elongate rigid endoscope shaft comprising an optics shaft with an imaging optics and an electronic image sensor is provided, a head piece having a head piece housing being arranged at a proximal end section of the endoscope shaft. Moreover, an electronics unit and a handle housing are provided, the handle housing being configured for accommodating the electronics unit. Electric connections between the electronics unit and the endoscope shaft are formed by means of electric connectors, for example plug connectors, and the electronics unit is mounted to the head piece housing with at least one first fixation element, for example by one or more screws. Thereafter the handle housing is mounted to the electronics unit, thereby covering the at least one first fixation element such that the at least one first fixation element is no longer accessible from the outside. The handle housing may be held to the electronics unit by a second fixation element, for example a coupling nut which preferably requires special tooling for being turned.

The electronics unit comprises electronic circuitry for supplying at least the electronic image sensor with electric energy, for controlling the electronic image sensor, and for pre-processing image data provided by the electronic image sensor. The head piece housing may comprise control elements for controlling various functions of the endoscope, and the control elements are electrically connected to the electronics unit by means of one or more electric connectors. The optics shaft and a plug connector housing arranged at a proximal end of the optics shaft form a hermetically sealed unit enclosing the imaging optics and the image sensor. The electronics unit also is hermetically sealed. The handle housing and the head piece housing are configured such that, when the handle housing is fixed to the electronics unit, a seal element is compressed between respective interfaces of the head piece housing and the handle housing. Thus, the video endoscope in total may form a sealed compartment, however, this compartment is not necessarily hermetically sealed.

In order to disassemble the video endoscope, the method steps described above are taken in inverted sequence. Thus, first the second fixation element is released which may require a special tool. Thereafter the handle housing is pulled off from the electronics unit, the at least one first fixation element is released, and the electronics unit is detached from the head piece housing. The handle housing, the electronics unit and the endoscope shaft, the endoscope shaft including the optics unit, can be separately cleaned and sterilized. Preferably, the video endoscope is autoclavable, its delicate optical and electronic components being enclosed in hermetically sealed chambers.

Due to the modular design of the video endoscope, the electronics unit can be attached to another endoscope shaft, or the endoscope shaft can be combined with another electronics unit. In this way a video endoscope having, for example, a different viewing angle can be configured employing the same electronics unit. Further, in case of repair of the electronics unit, the electronics unit can be easily replaced with another electronics unit, without the need to replace the complete video endoscope.

The features of the invention as mentioned above and as described below apply not only in the combinations mentioned but also in other combinations or alone, without leaving the scope of the present invention.

BRIEF DESCRIPTION OF THE DRAWINGS

Further aspects of the present invention will be apparent from the figures and from the description of a particular embodiment that follows.

DETAILED DESCRIPTION OF THE INVENTION

Figure 1:
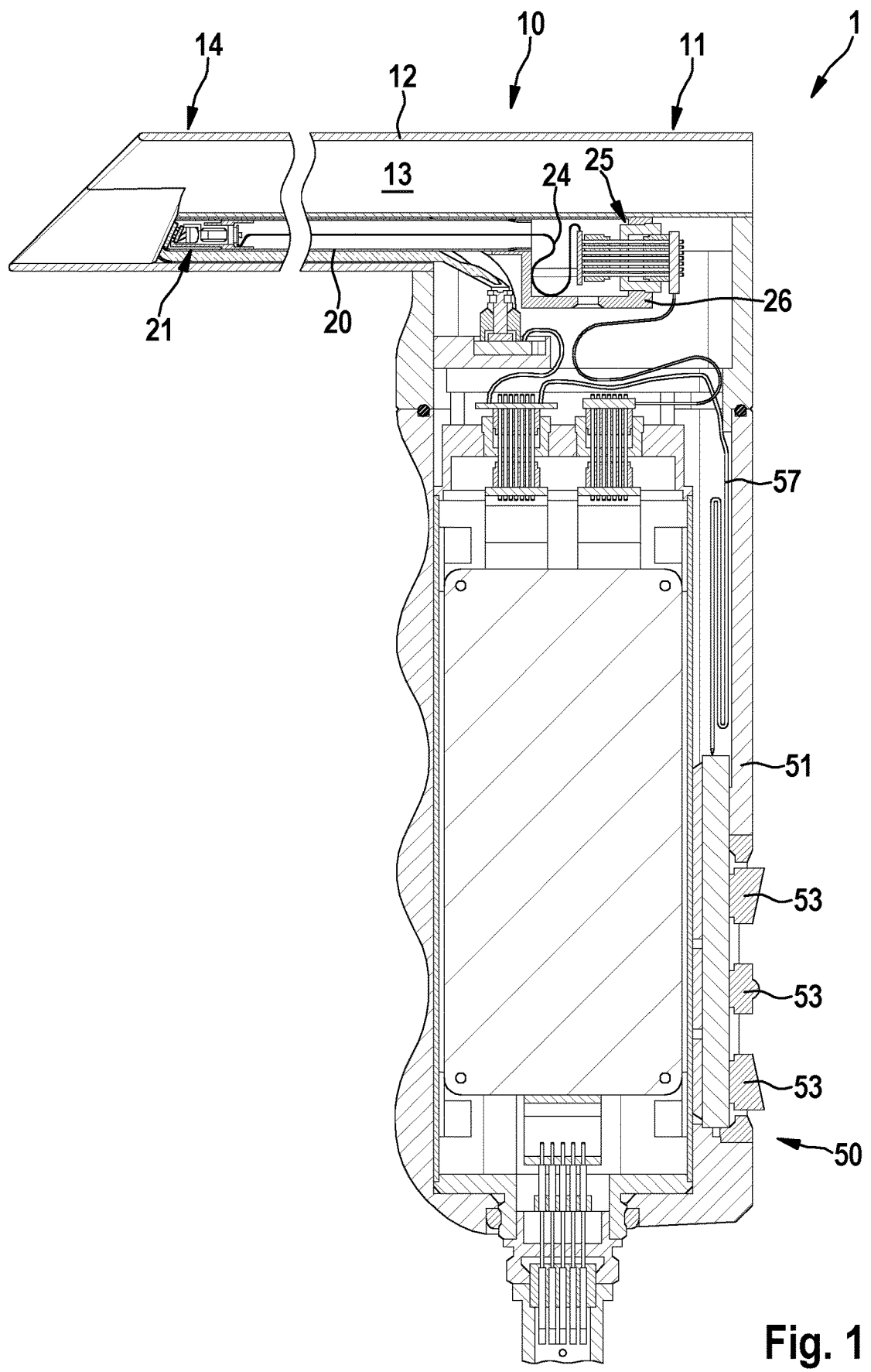
FIG. 1 shows a video endoscope according to an embodiment of the present invention in an axial sectional view.

The exemplary embodiment of the video endoscope shown in the figures is a video mediastinoscope 1. As is shown in FIG. 1 in a partially cut-open longitudinal sectional view, the video mediastinoscope 1 comprises an elongate shaft 10 and a handle 50 attached to a proximal end section 11 of the shaft 10, the shaft 10 being configured for being introduced through an incision into the mediastinum of a patient. The shaft 20 may have a length of about 10-40 cm, for example approximately 20 cm. The shaft 10 is formed by an approximately cylindrical shaft tube 12 comprising a longitudinal end-to-end slot. The shaft tube 12 encloses a longitudinal hollow space 13 configured for inserting instruments such as for taking biopsies, for example. At its lower inner side the shaft tube 12 has a longitudinal thickening that comprises a longitudinal bore into which a tube-like optics shaft 20 is inserted. The optics shaft 20 is fixedly connected to the shaft tube 12, for example by soldering or with an adhesive. Within the optics shaft 20 an imaging unit 21 is arranged in a distal end section of the optics shaft 20, the imaging unit comprising an objective lens 22 and an electronic image sensor 23. The image signal generated by the image sensor 23 is transmitted by a flexible printed circuit board (flexible PCB 24) to a plug connector 25 arranged at a proximal end of the optics shaft 20.

The optics shaft 20 preferably is an approximately cylindrical metallic tube. At its proximal end the optics shaft 20 is connected to a plug connector housing 26 in which the plug connector 25 is inserted in a hermetically sealed manner, for example by welding (see FIG. 2). The plug connector 25 is a glass-mold plug connector, for example, having a multiplicity of connecting pins 29 being sealingly soldered with glass solder into and penetrating a glass base 25*a* of the plug connector 25. A proximal end section of the optics shaft 20 is inserted into a tube-like distal section 26*a* of the plug connector housing 26, being fixed to and hermetically sealed in the distal section 26*a* by soldering or welding, for example. At its distal end the optics shaft 20 is closed by a cover glass 27 that is inserted into the distal end section of the tube-like optics shaft 20 in a hermetically sealed manner, for example by soldering or by a suitable adhesive. The optics shaft 20 and the plug connector housing 26 form a hermetically sealed unit, enclosing a hermetically sealed chamber in which the objective lens 22, the electronic image sensor 23 and the flexible PCB 24 are housed. The plug connector housing 26 has a bore 26*b* for leak checking, the bore 26*b* being hermetically closed by a lid welded into a widening on an exterior side of the bore 26*b*. Further details of the optics shaft 20, the plug connector housing 26 and the electric and electronic components enclosed therein are disclosed in the co-pending German patent application number 102019003842.8, filed Jun. 3, 2019, and entitled "Endoscope and method for manufacturing an endoscope" which is incorporated herein by reference.

Figure 2:
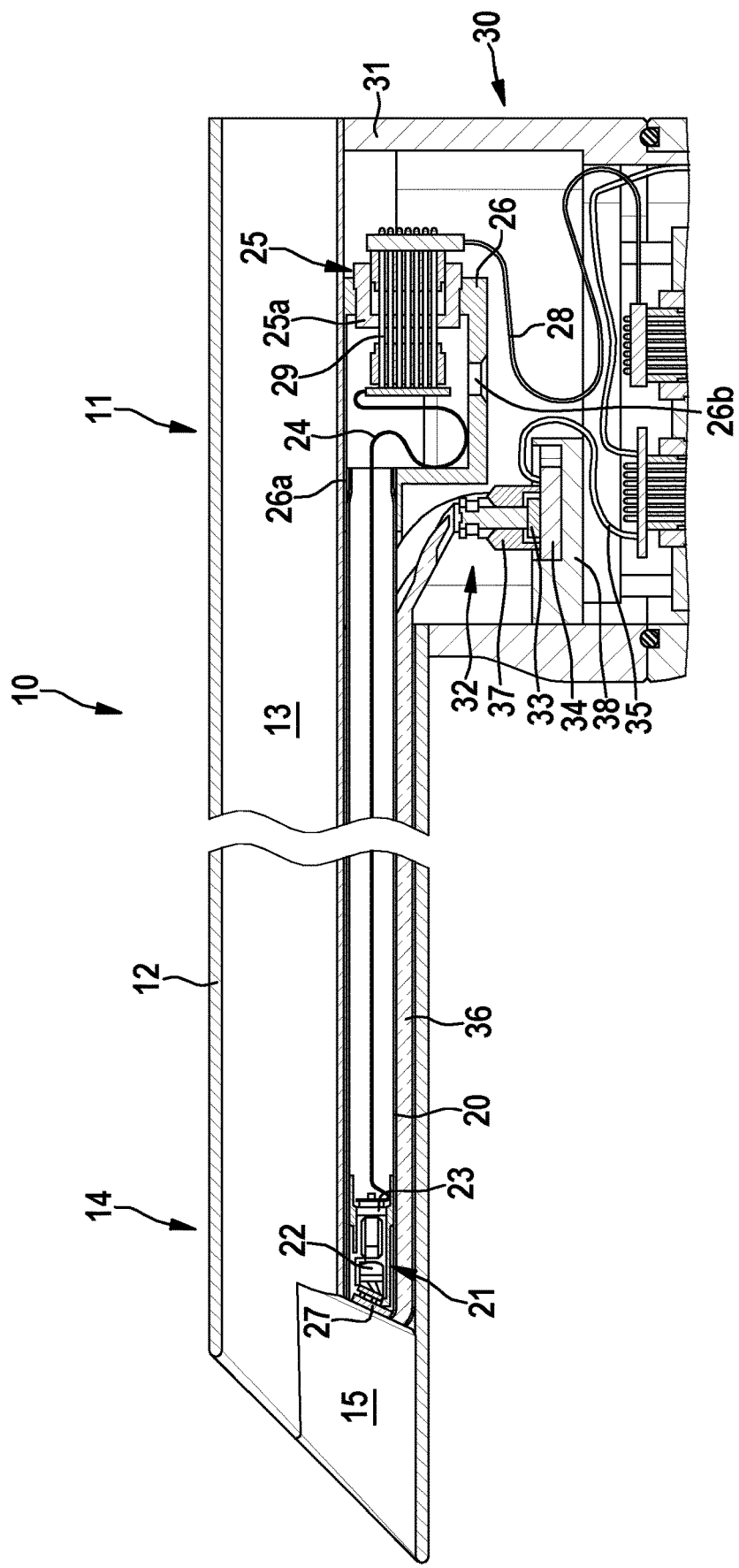
FIG. 2 shows an enlarged axial sectional view of the shaft and the head piece of the video endoscope of FIG. 1.

Further it is shown in FIGS. 1 and 2 that a head piece 30 is fixed to the shaft tube 12 in the proximal end section 11 of the shaft 10. The head piece 30 has a head piece housing 31 in which the plug connector housing 26 and a light source 32 are enclosed. Further the head piece housing 31 accommodates electric leads (see below). The head piece housing 31 is fixed to the shaft tube 12 in a not detachable manner by soldering or welding, for example, and can thus be considered a part of the shaft 10 of the video mediastinoscope 1. The light source 32 comprises an LED 33 mounted on an LED board 34 and contacted to electric leads 35. A light guide 36 formed by a glass fiber bundle is optically coupled to the LED 33. Illumination radiation generated by the LED 33 is transmitted by the light guide 36 until the distal end section 14 of the shaft 10, where the illumination radiation exits from the glass fibers for illuminating an object field to be observed and/or the working space 15. A proximal end section of the bundle of glass fibers is held in a fiber mount 37. The LED board 34 is mounted on a metallic carrier element 38 mounted to an inner side of the head piece housing 31. The LED 33, the LED board 34 and the proximal end of the bundle of glass fibers are embedded in a sealing compound (not shown).

Figure 3:
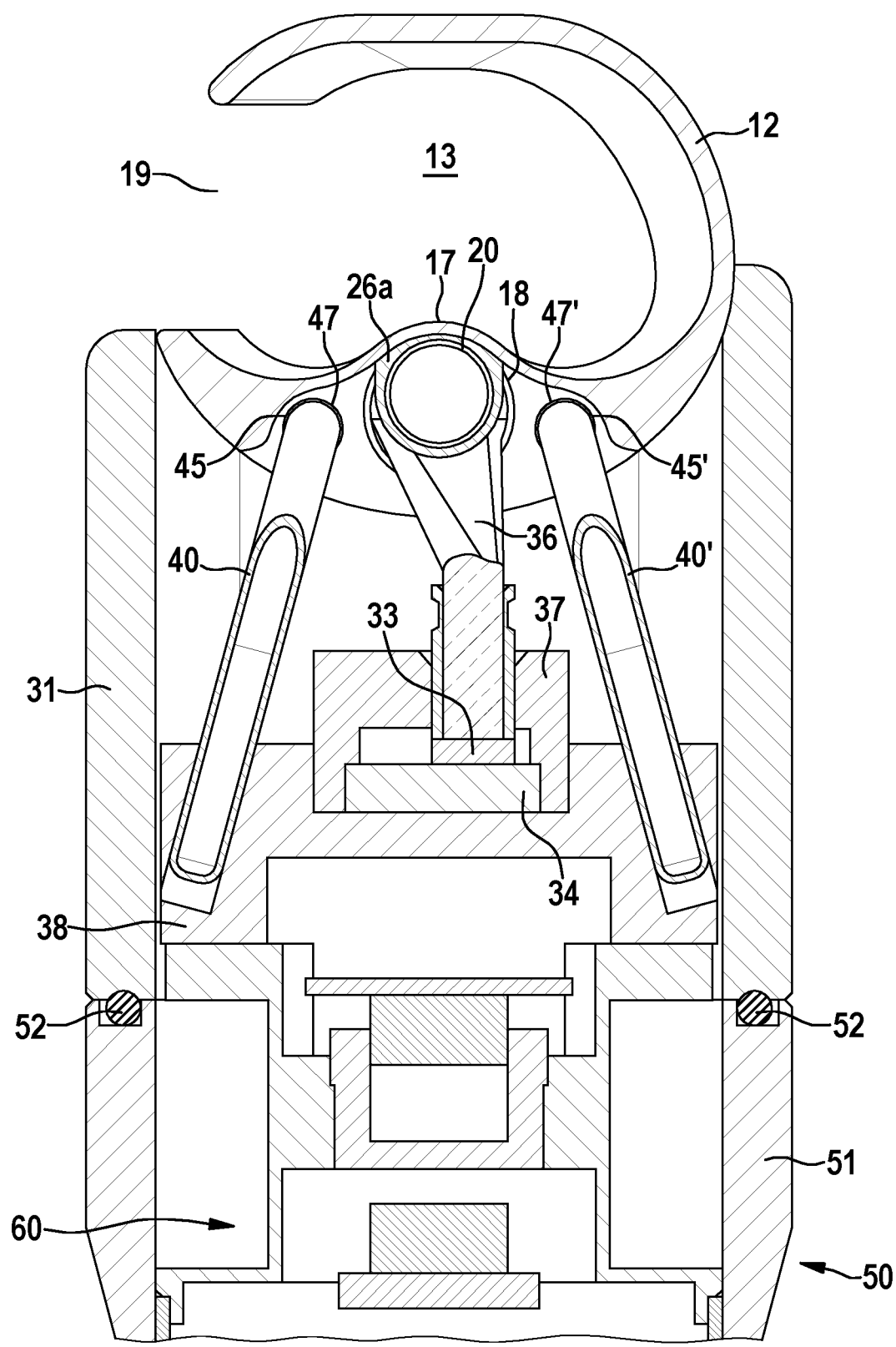
FIG. 3 shows a cross section through the shaft and the head piece of the video endoscope of FIG. 1.

FIG. 3 shows a cross-sectional view, as seen from a proximal direction, through the shaft 10, the head piece 30 and the LED 33. As depicted in FIG. 3, the LED 33 is optically coupled to the light guide 36, a proximal end of the glass fiber bundle forming the light guide 36 being held in the fiber mount 37. The light guide 36 extends through the shaft tube 12 of the shaft 10 in a distal direction, the glass fibers being arranged below and laterally of the optics shaft 20. The LED 33 is mounted on the LED board 34, the LED board 34 being mounted in a heat-conducting manner to the carrier element 38. Heat pipes 40, 40' are inserted into bores of the carrier element 38 and thermally coupled to the carrier element 38 by heat-conducting adhesive. Excess heat generated by the LED 33 during operation is conducted via LED board 34 to the carrier element 38 and, to a major fraction, transported into the shaft 10 by the heat pipes 40, 40'. A minor fraction of the excess heat is conducted by the carrier element 38 directly into the head piece housing 31. Details of the heat management of the video mediastinoscope 1 are described in the above mentioned co-if) pending German Patent Application No. 102019003839.8, "Endoskop, Verfahren zum Betreiben eines Endoskops sowie Verfahren zum Herstellen eines Endoskops".

As is also depicted in FIG. 3, the shaft tube 12 of the shaft 10 is approximately cylindrical, having a flattened upper side in its proximal end section and a longitudinal slit 19. In its lower part the shaft tube 12 comprises a thickening formed by a longitudinally extending bead 17 formed on an inner side of the shaft tube 12. The shaft tube 12 comprises a longitudinal bore 18 and two lateral dead-end bores 45, 45' in which the heat pipes 40, 40' are embedded in heat-conducting adhesive 47, 47'. The longitudinal bore 18 accommodates the optics shaft 20 and the light guide 36, the optics shaft 20 accommodating the imaging unit 21 and the flexible PCB 24 (not shown in FIG. 3). Further it can be seen in FIG. 3 that a handle housing 51 of the handle 50 is attached to the head piece housing 31, a sealing element 52 being compressed in between. The handle housing 51 and the head piece housing 31 are shaped in conjunction to be gripped by a user with one hand (see FIG. 1).

Figure 4:
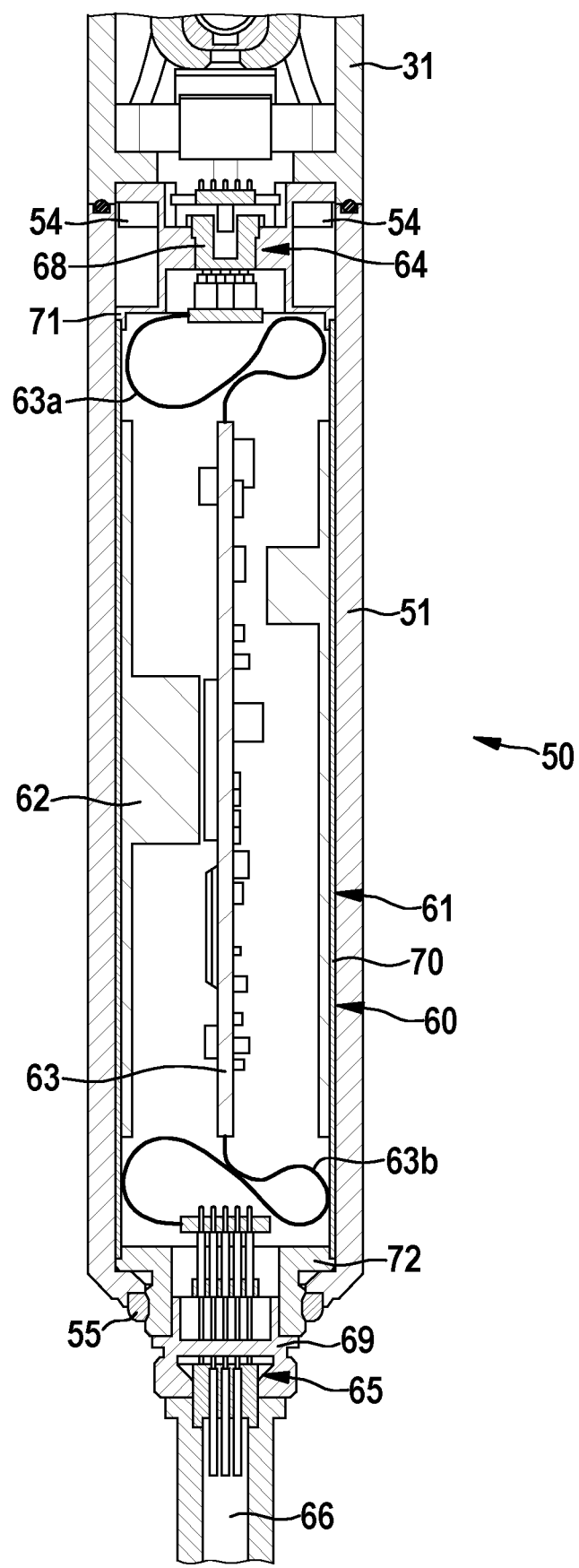
FIG. 4 shows a cross section through the lower part of the handle of the video endoscope of FIG. 1.

FIG. 4 shows a cross section of the handle 50, the cross sectional view approximately forming a continuation of the cross sectional view shown in FIG. 3. The handle housing 51 of the handle 50 accommodates an electronics unit 60. The electronics unit 60 has a metallic casing 61 enclosing a carrier 62 preferably formed of aluminum and an electronics board. The electronics board, which is briefly denoted supply board 63, comprises electronic circuitry for supplying the LED 33 and the electronic image sensor 23 with electric energy, for controlling the LED 33 and the electronic image sensor 23, as well as for image pre-processing of the image signals received from the electronic image sensor 23. To this end the supply board 63 is electrically connected via electric leads 64*a*, plug connectors 64 and electric leads 28, 35 with the image sensor 23 and the LED 33, respectively (see FIG. 2). Further the supply board 63 is electrically connected via plug connector 64 and electric leads 57 with a multiplicity of control buttons 53 arranged on a proximal side of the handle housing 51 (see FIGS. 1 and 2). The control buttons 53 permit control of various functions of the mediastinoscope 1, such as illumination and electronic zoom. Furthermore the supply and control board 63 is connected via electric leads 63*b* and plug connector 65 with electric lines 66 for connecting the mediastinoscope 1 to an external supply and processing system that may comprise a monitor for displaying the endoscopic image as well as further control elements. The electric leads 28, 35, 63*a*, 63*b* may be formed by flexible circuit boards or ribbon cables, for example.

The shape of the carrier 62 is adapted to the circuitry of the supply board 63 and, for example, has a sufficient thickness to substantially fill the space formed between the casing 61 and the supply board 63 at least in such sections of the supply board 63 in which most excess heat is generated. The supply board 63 is coupled thermally to the carrier 62 by heat conducting paste or adhesive, and the carrier 62 is coupled thermally by heat conduction paste or adhesive to the casing 61. The casing 61 is thermally coupled to the handle housing 51 by plane contact and, possibly, by heat conducting paste.

The electronics unit 60 is hermetically sealed. To this end the plug connectors 64, 65 are inserted into the metallic casing 61 in a hermetically sealed manner. As is indicated in FIG. 4, the plug connectors 64, 65 each comprise a plug connector insert 68, 69 penetrated by a multiplicity of pins in a sealed manner. Thus, for example, the plug connector inserts 68, 69 may be formed as glass-mold inserts. The casing 61 may be formed as one piece of a metallic material, into which the plug connector inserts 68, 69 are inserted in a hermetically sealed manner, for example by welding. In the embodiment depicted in FIG. 4 the casing 61 is formed by a metallic main part 70, an upper lid element 71 and a lower lid element 72, which are connected to the main part 70 in a hermetically sealed manner, for example by welding, soldering or gluing with a suitable adhesive. The plug connector insert 68 of the plug connector 64 is inserted in a hermetically sealed manner into the upper lid element 71 of the casing 61, and the plug connector insert 69 of the plug connector 65 is hermetically sealed inserted into the lower lid element 72 of the casing 61. In this way the supply board 63 is enclosed in a hermetically sealed chamber, such that the electronics unit 60 forms a hermetically sealed unit. The supply board 63 is thus perfectly protected against intrusion of moisture.

As is further shown in FIG. 4, the electronics unit 60 is fixed by screws 54 to the head piece housing 61. The screws 54, however, are covered by the handle housing 51 and are not accessible from the outside as long as the handle housing 51 is attached to the head piece housing 31. The handle housing 51 of the handle 50 is held to the electronics unit 60 by a coupling nut 55. The coupling nut 55 is configured to be operable only with a special tool, for example the coupling nut 55 may have three grooves separated by 120° into which a correspondingly shaped tool may be inserted for turning the coupling nut 55.

In order to detach the handle 50 from the shaft 10 and to replace the electronics unit 60, the supply cable comprising the electric lines 66 is pulled off from plug connector 65, the coupling nut 55 is released, and thereafter the handle housing 51 of the handle 50 is pulled off from the casing 61 of the electronics unit 60. Now the screws 54 have become accessible and are loosened. After unplugging the plug connectors 64, 65 the electronics unit 60 is detached from the shaft 10. The electronics unit 60 can now be replaced by another electronics unit, which can be connected electrically and mechanically to the respective components of the shaft 10 by corresponding steps in inverted order.

For clarity not all reference numerals are displayed in all figures. If a reference numeral is not explicitly mentioned in the description of a figure, it has the same meaning as in the other figures.

REFERENCE NUMERALS

1 Mediastinoscope
10 Shaft
11 Proximal end section
12 Shaft tube
13 Hollow space
14 Distal end section
15 Working space
17 Bead
18 Longitudinal bore
19 Slit
20 Optics shaft
21 Imaging unit
22 Objective lens
23 Image sensor
24 Flexible PCB
25 Plug connector
25a Base
26 Plug connector housing
26a Distal section
26b Bore
27 Cover glass
28 Electric leads
29 Pin
30 Head piece
31 Head piece housing
32 Light source
33 LED
34 LED board
35 Electric leads
36 Light guide
37 Fiber mount
38 Carrier element
40, 40' Heatpipe
45, 45' Dead-end bore
47, 47' Heat-conductive adhesive
50 Handle
51 Handle housing
52 Sealing element
53 Control button
54 Screw
55 Coupling nut
57 Electric leads
60 Electronics unit
61 Casing
62 Carrier
63 Supply board
63a Electric leads
63b Electric leads
64 Plug connector
65 Plug connector
66 Supply lines
68 Plug connector insert
69 Plug connector insert
70 Main part
71 Upper lid element
72 Lower lid element

The invention claimed is:

1. A video mediastinoscope comprising:
an elongate rigid shaft including an optics shaft including an imaging optics and an electronic image sensor, wherein the optics shaft and a plug connector housing are disposed on a proximal end of the elongate rigid shaft, the optics shaft and the plug connector housing hermetically enclosing the imaging optics and the image sensor to define a hermetically sealed unit;
a handle detachably attached to a proximal end section of the elongate rigid shaft, the handle including a handle housing in which an electronics unit is accommodated, the handle housing including a metallic casing enclosing the electronics unit so as to form a hermetically sealed unit that is independent of the hermetically sealed optics shaft; and
wherein the elongate rigid shaft includes a shaft tube to which the optics shaft is rigidly connected, and wherein the shaft tube includes a slit extending from a distal end to the proximal end of the shaft tube, and further comprises a hollow space configured for inserting instruments therethrough.

2. The video mediastinoscope of claim 1, wherein the proximal end of the shaft tube further comprises a head piece rigidly connected to the proximal end of the shaft tube, and wherein both the electronics unit and the handle housing are independently detachably attached to the head piece of the shaft tube of the video mediastinoscope.

3. The video mediastinoscope of claim 2, wherein at least one plug connector is hermetically integrated into the plug connector housing.

4. The video mediastinoscope of claim 3, wherein at least one plug connector is hermetically integrated into the metallic casing of the electronics unit.

5. The video mediastinoscope of claim 2, wherein the handle housing is detachably fixed to the electronics unit and the electronics unit is detachably fixed to the head piece with at least one first fixation element, the at least one first fixation element being accessible only when the handle housing has been detached from the electronics unit.

6. The video mediastinoscope of claim 5, wherein the shaft of the video mediastinoscope comprises at least one light source arranged outside the optics shaft and the plug connector housing, and that the shaft of the video endoscope comprises at least one light guide for transmitting illumination radiation generated by the light source to a distal end section of the shaft, a proximal end section of the at least one light guide being optically coupled to the light source, and wherein the proximal end section of the at least one light guide and the light source are both embedded in a sealing compound.

7. The video mediastinoscope of claim 6, wherein the handle housing comprises at least one manually activated control element electrically connected to the electronics unit and/or to the electronic image sensor and/or to the light source, the at least one manually activated control element located outside of the electronics unit.

8. The video mediastinoscope of claim 2, further including plug connectors inserted into the metallic casing.

9. The video mediastinoscope of claim 8, wherein the metallic casing is formed as one piece and the plug connectors are hermetically inserted into the metallic casing.

10. The video mediastinoscope of claim 1, wherein at least one plug connector is hermetically integrated into the plug connector housing.

11. The video mediastinoscope of claim 1, wherein at least one plug connector is hermetically integrated into the metallic casing of the electronics unit.

12. The video mediastinoscope of claim 1, wherein the shaft of the video mediastinoscope comprises at least one light source arranged outside the optics shaft and the plug connector housing, and that the shaft of the video endoscope comprises at least one light guide for transmitting illumination radiation generated by the light source to a distal end section of the shaft, a proximal end section of the at least one light guide being optically coupled to the light source, and wherein the proximal end section of the at least one light guide and the light source are both embedded in a sealing compound.

13. The video mediastinoscope of claim 12, wherein the handle housing comprises at least one manually activated control element electrically connected to the electronics unit and/or to the electronic image sensor and/or to the light source, the at least one manually activated control element located outside of the electronics unit.

14. The video mediastinoscope of claim 13, wherein the shaft of the video mediastinoscope and the handle attached to the shaft forms a sealed unit.

15. The video mediastinoscope of claim 14, wherein the video mediastinoscope is configured to be autoclavable.

16. The video mediastinoscope of claim 1, wherein the shaft of the video mediastinoscope and the handle attached to the shaft forms a sealed unit.

17. The video mediastinoscope of claim 16, wherein the video mediastinoscope is configured to be autoclavable.

* * * * *